United States Patent [19]

Kuwada et al.

[11] 4,013,763
[45] Mar. 22, 1977

[54] HETEROCYCLIC COMPOUNDS

[75] Inventors: Yutaka Kuwada; Kanji Meguro; Hideaki Natsugari; Yoshiaki Sato, all of Hyogo; Hiroyuki Tawada, Osaka, all of Japan

[73] Assignee: Takeda Chemical Industries, Ltd., Osaka, Japan

[22] Filed: July 3, 1975

[21] Appl. No.: 592,814

[30] Foreign Application Priority Data

July 12, 1974 Japan .......................... 49-80646
July 25, 1974 Japan .......................... 49-85787

[52] U.S. Cl. .......................... 424/246; 260/243 R; 260/244 R; 260/251 A; 260/294.8 A; 260/296 R; 260/296 P; 424/251; 424/263; 424/248.4; 424/248.58

[51] Int. Cl.² ...................... C07D 491/22

[58] Field of Search ............... 260/244 R, 294.8 A, 260/296 P, 243 R, 251 A; 424/248, 263

[56] References Cited

UNITED STATES PATENTS 3,883,544  5/1975  Hester et al. .................. 260/296 R

FOREIGN PATENTS OR APPLICATIONS 2,153,519  5/1972  Germany

*Primary Examiner*—Cecilia M.S. Jaisle
*Attorney, Agent, or Firm*—Burgess, Ryan and Wayne

[57] ABSTRACT

A novel heterocyclic compound of the general formula:

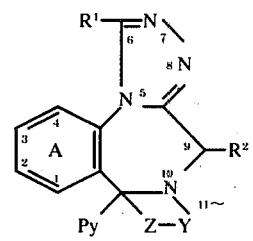

wherein $R^1$ represents hydrogen atom or a hydrocarbon residue; $R^2$ represents hydrogen atom or a lower alkyl group; Py represents a pyridyl group; Y represents an ethylene or a trimethylene group which may have lower alkyl group as substituent; Z represents oxygen atom, sulfur atom or —NH— groups; and the ring A is either unsubstituted or substituted by a halogen atom, nitro, alkyl, alkoxy or trifluoromethyl group, is found to be useful as medicine in human and animal therapy, as these compounds act on the central nervous system, as, for example, muscle relaxants, anticonvulsants, sedatives, minor tranquilizers, etc.

27 Claims, No Drawings

HETEROCYCLIC COMPOUNDS

This invention relates to novel heterocyclic compounds useful as medicines represented by the general formula (I):

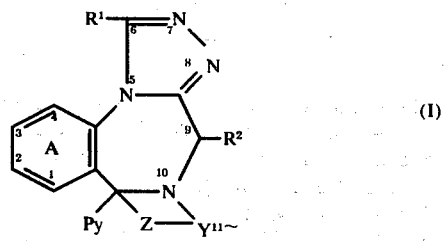

wherein $R^1$ represents hydrogen atom or a hydrocarbon residue; $R^2$ represents hydrogen atom or a lower alkyl group; Py represents a pyridyl group; Y represents an ethylene or a trimethylene group which may have lower alkyl group as substituent; Z represents oxygen atom, sulfur atom or —NH— group; and the ring A is either unsubstituted or substituted by a halogen atom, nitro, alkyl, alkoxy or trifluoromethyl group, and to a process for producing the same.

The present invention is further concerned with a novel compound having the following general formula (II) which is useful as intermediate for the production of heterocyclic compounds of the general formula (I):

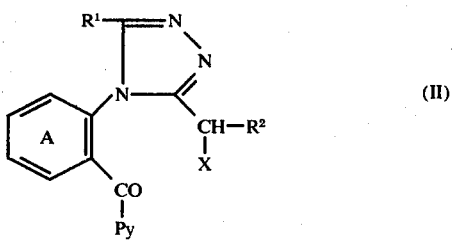

wherein $R^1$, $R^2$, Py and the ring A have the same meanings as defined above and X represents halogen atom or an active ester residue of a hydroxy group.

The compound (I) has pharmacological effects acting on the central nervous system such as muscle relaxant, anticonvulsant, sedative, antianxiety, tranquilizing and sleep inducing effects and are useful as medicines in human and animal therapy such as muscle relaxants, anticonvulsants, sedatives, antianxiety agents, minor tranquilizers and hypnotics.

In the aforesaid formulae, the hydrocarbon residue represented by $R^1$ includes alkyl, aralkyl and aryl groups. The alkyl groups are preferably lower alkyl groups having 1 to 6 carbon atoms, and the alkyl group may be a straight, branched or cyclic one. Examples of such alkyl groups include methyl, ethyl, propyl, isopropyl, butyl, isobutyl, sec-butyl, tert-butyl, pentyl, hexyl, cyclopropylmethyl, cyclopentyl and cyclohexyl groups. The aralkyl groups are exemplified by benzyl, phenethyl, etc.; and the aryl groups are exemplified by phenyl, tolyl, naphthyl, etc. As the group represented by $R^1$, hydrogen atom and a lower alkyl group having 1 to 3 carbon atoms are particularly preferred.

The lower alkyl group represented by $R^2$ is preferably one having 1 to 4 carbon atoms, and includes, for example, methyl, ethyl, propyl, isopropyl, butyl, isobutyl, sec-butyl, and tert-butyl groups.

When the ring A is substituted by a halogen atom or nitro, alkyl, alkoxy or trifluoromethyl group, the number of said substituents is optional at any substitutable position of the ring A. The halogen atom which is the substituent of the ring A includes fluorine, chlorine, bromine and iodine. The lower alkoxy group which is the substituent of the ring A includes, for example, lower alkoxy groups having 1 to 4 carbon atoms such as methoxy, ethoxy, propoxy and butoxy groups. The alkyl group which is the substituent of the ring A includes, for example, the same lower alkyl groups having 1 to 4 carbon atoms as those represented by $R^2$. As the position of the substituent of the ring A in the formula (I), 2-position of the formula (I) is preferable, and 2-halogen atom, especially 2-bromo and 2-chloro atoms are preferred as the substituent of the ring A.

The pyridyl groups represented by Py is represented by the formula

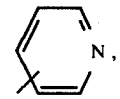

and, among them, the 2-pyridyl group is preferred.

When the ethylene and trimethylene groups represented by Y has a lower alkyl group as substituent, the said alkyl group includes lower alkyl groups having 1 to 4 carbon atoms such as those represented by $R^2$.

As the group represented by Z, the oxygen atom is preferred.

In the formulae described hereinafter, the ring A, $R^1$, $R^2$, Y, Z and Py have the same meanings as defined above.

The compounds of the formula (I) can be produced by a process which comprises reacting a compound represented by the general formula (II):

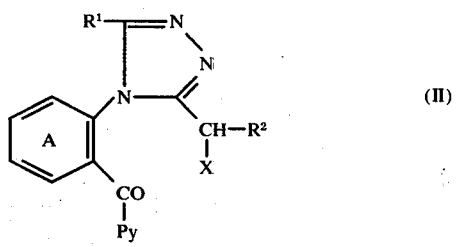

wherein X represents a halogen atom or an active ester residue of a hydroxy group, with a compound represented by the general formula (III):

$$HZ-Y-NH_2 \qquad (III)$$

In the above formula (II), the halogen atom represented by X includes those as represented by the substituent on the ring A (i.e. chlorine, bromine, iodine and fluorine atoms). The active ester residue of the hydroxy group represented by X is exemplified by sulfoxy (—OSO₃H) group, alkyl sulfonyloxy group such as methyl sulfonyloxy group, aryl sulfonyloxy group such as phenyl sulfonyloxy group, p-tolyl sulfonyloxy group, etc.

The process for producing the compound (I) is carried out by reacting the compound (II) with the compound (III). The amount of the compound (III) to be used is ordinarily about 1 to 10 moles per mole of the compound (II). The reaction may proceed in the absence of a solvent, but proceeds more smoothly in the presence of a solvent. Examples of such solvents are alcohols (e.g. methanol, ethanol, propanol, butanol, etc.), aliphatic, aromatic or halogenated hydrocarbons (e.g. benzene, toluene, xylene, chloroform, dichloromethane, etc.), dialkylformamides (e.g. dimethyl- or diethylformamide, etc.), phenols, etc. The reaction temperature is within the range of room temperature to about 200° C. When a solvent is used, the reaction temperature is usually around the boiling point of the solvent used.

When X of the compound (II) is a halogen atom, a hydrogen halide corresponding to X is produced in this reaction. In order to accept the hydrogen halide, the compound (III) may be used in excess, or alternatively there may be added to the reaction system a suitable basic substance (e.g. a tertiary amine such as triethylamine or pyridine, or an alkali metal carbonate or hydrogen carbonate such as sodium carbonate, potassium carbonate, sodium hydrogen carbonate or potassium hydrogen carbonate). When a compound (II), wherein X is chlorine or bromine atom, is used as the starting material, the reaction may be more smoothly carried out in the presence of a catalytic or equimolar amount of potassium iodide or sodium iodide.

The compounds (II), can be produced according to, for example, the procedure as shown by the following reaction scheme:

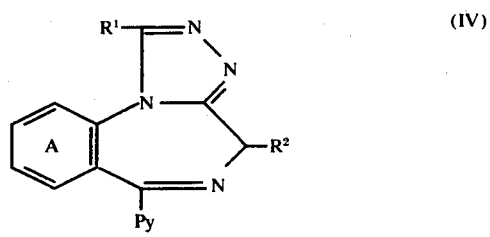

wherein $R^1$, $R^2$, Py and the ring A are as defined above, with nitrous acid or its alkali metal salt in the presence of a hydrohalogenic acid. The compound (IV) can be produced according to the similar method to those disclosed in Japanese Patent Application Laid Open No. 42798/1972 and Dutch Patent Application Laid Open No. 7309733.

Examples of hydrohalogenic acids to be used in this reaction are hydrochloric acid, hydrobromic acid and hydroiodic acid. The alkali metal salts of nitrous acid are, for example, salts of nitrous acid with sodium, potassium etc. The hydrohalogenic acid and the alkali metal salt of nitrous acid are used usually in excess relative to the compound (IV). For example, it is preferred to use at least 3 mole equivalents of hydrohalogenic acid and about 1 to 20 times moles of nitrous acid or its alkali metal salt. The reaction is generally carried out at 0° to 30° C. Since the hydrohalogenic acid or the alkali metal salt of nitrous acid is usually used in the form of an aqueous solution thereof, no other solvent is specifically required.

When hydrohalogenic acid is replaced by a mineral

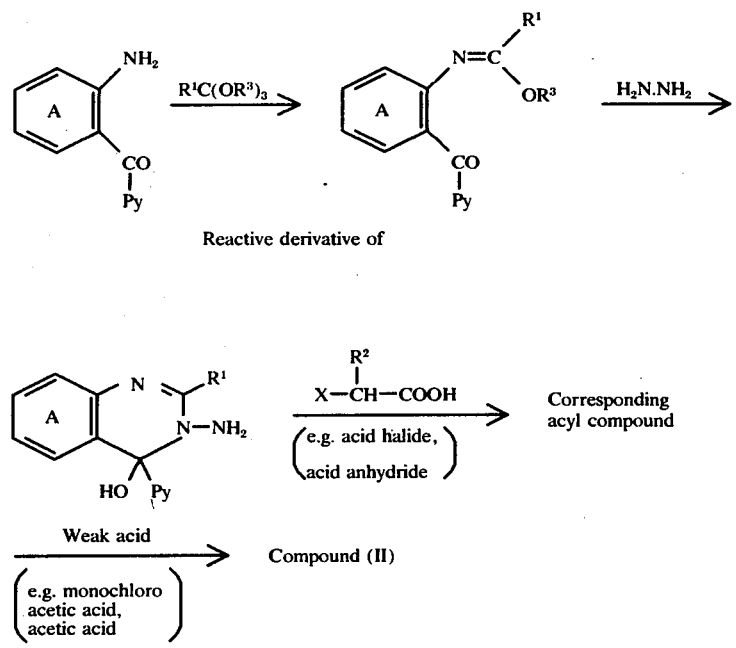

wherein $R^1$, $R^2$, X, Py and the ring A are as defined above, and $R^3$ represents lower alkyl group (e.g. methyl, ethyl, propyl group).

Further, the compound (II) wherein X is halogen atom is obtained together with that wherein X is hydroxy group by reacting the compound of the general formula (IV):

acid (e.g. sulfuric acid) or an organic acid (e.g. acetic acid) in the above reaction, there is generally obtained the compound (II) wherein X is hydroxy group.

The thus obtained mixture of compound (II) wherein X is hydroxy group and that wherein X is halogen atom or compound (II), wherein X is hydroxy group, is isolated by per se known methods (e.g. column chromatography or recrystallization) is treated with a halogenating agent such as thionyl chloride, phosphorus halide (e.g. phosphorus trichloride, phosphorus tribromide, phosphorus pentachloride or phosphorus pentabromide), or an esterifying agent such as alkyl sulfonyl chloride (e.g. methane sulfonyl chloride), or aryl sulfonyl chloride (e.g. benzene sulfonyl chloride, paratoluene sulfonyl chloride) to give the compound (II). These halogenation or esterification reactions are usually carried out in an inert solvent (e.g. chloroform, ethyl ether or benzene) by using equimolar or more amounts (e.g. about 1 to 20 times moles) of the reagents at about 0° to 30° C. The thus produced compounds (II) can be isolated with desired purity by conventional separation or purification methods such as recrystallization or chromatography.

When the object compounds (I) of the present invention are used as medicines in human and animal therapy such as muscle relaxants, anticonvulsants, sedatives, antianxiety agents, minor tranquilizers or hypnotics, they may be orally or parenterally administered as such or in a suitable form such as powders, granules, tablets, capsules, injections, suppository etc. admixed with pharmaceutically acceptable carriers, excipients or diluents. The dose of the compound (I) to be administered varies with the kinds of diseases to be treated, the clinical conditions and the kind of the compound to be used, but usually falls within the range of from about 1 to 100 mg. for oral administration for an adult human per day.

Specific compounds as represented by the general formula (I) and (II), inclusive of those as shown in Examples which are set forth for illustrative but not limiting purpose, are as follows:

COMPOUND (I)

2-Bromo-11,12-dihydro-13a-(2-pyridyl)-9H,13aH-oxazolo[3,2-d]-s-triazolo[4,3-a][1,4]benzodiazepine;

2-Bromo-11,12-dihydro-11-methyl-13a-(2-pyridyl)-9H,13aH-oxazolo[3,2-d]-s-triazolo[4,3-a][1,4]benzodiazepine;

2-Bromo-11,12-dihydro-12-methyl-13a-(2-pyridyl)-9H,13aH-oxazolo[3,2-d]-s-triazolo[4,3-a][1,4]benzodiazepine;

2-Bromo-12,13-dihydro-14a-(2-pyridyl)-9H,11H,14aH-[1,3]-oxazino[3,2-d]-s-triazolo[4,3-a][1,4]benzodiazepine;

2-Bromo-11,12-dihydro-13a-(2-pyridyl)-9H,13aH-thiazolo-[3,2-d]-s-triazolo[4,3-a][1,4]benzodiazepine;

2-Bromo-11,12-dihydro-13a-(4-pyridyl)-9H,13aH-oxazolo-[3,2-d]-s-triazolo[4,3-a][1,4]benzodiazepine;

2-Bromo-11,12-dihydro-9-methyl-13a-(2-pyridyl)-9H,13aH-oxazolo[3,2-d]-s-triazolo[4,3-a][1,4]benzodiazepine;

2-Bromo-11,12-dihydro-6-methyl-13a-(2-pyridyl)-9H,13aH-oxazolo[3,2-d]-s-triazolo[4,3-a][1,4]benzodiazepine;

2-Bromo-11,12-dihydro-6,11-dimethyl-13a-(2-pyridyl)-9H,13aH-oxazolo[3,2-d]-s-triazolo[4,3-a][1,4]benzodiazepine;

2-Bromo-11,12-dihydro-6,12-dimethyl-13a-(2-pyridyl)-9H,13aH-oxazolo[3,2-d]-s-triazolo[4,3-a][1,4]benzodiazepine;

2-Bromo-12,13-dihydro-6-methyl-14a-(2-pyridyl)-9H,11H,14aH-[1,3]oxazino[3,2-d]-s-triazolo[4,3-a][1,4]benzodiazepine;

2-Bromo-11,12-dihydro-6-ethyl-13a-(2;1-pyridyl)-9H,13aH-oxazolo-[3,2-d]-s-triazolo[4,3-a][1,4]benzodiazepine;

2-Bromo-11,12-dihydro-6-ethyl-11-methyl-13a-(2-pyridyl)-9H,13aH-oxazolo[3,2-d]-s-triazolo[4,3-a][1,4]benzodiazepine;

2-Bromo-11,12-dihydro-6-ethyl-12-methyl-13a-(2-pyridyl)-9H, 13aH-oxazolo[3,2-d]-s-triazolo[4,3-a][1,4]benzodiazepine;

2-Bromo-11,12-dihydro-6-n-propyl-13a-(2-pyridyl)-9H,13aH-oxazolo[3,2-d]-s-triazolo[4,3-a][1,4]benzodiazepine;

2-Bromo-11,12-dihydro-6-isoproyl-(2-pyridyl)-9H,13aH-oxazolo[3,2-d]-s-triazolo[4,3-a][1,4]benzodiazepine;

2-Bromo-6-n-butyl-11,12-dihydro-13a-(2-pyridyl)-9H,13aH-oxazolo[3,2-d]-s-triazolo[4,3-a][1,4]benzodiazepine;

2Bromo-11,12-dihydro-6-phenyl-13a-(2-pyridyl)-9H,13aH-oxazolo[3,2-d]-s-triazolo[4,3-a][1,4]benzodiazepine;

6-Benzyl-2-bromo-11,12-dihydro-13a-(2-pyridyl)-9H,13aH-oxazolo[3,2-d]-s-triazolo[4,3-a][1,4]benzodiazepine;

2-Bromo-11,12,13,13a-tetrahydro-6-methyl-13a-(2-pyridyl)-9H-imidazo[1,2-d]-s-triazolo[4,3-a][1,4]benzodiazepine;

2-Chloro-11,12-dihydro-13a-(2-pyridyl)-9H,13aH-oxazolo-[3,2-d]-s-triazolo[4,3-a][1,4]benzodiazepine;

2-Chloro-11,12-dihydro-11-methyl-(2-pyridyl)-9H,13aH-oxazolo-[3,2-d]-s-triazolo[4,3-a][1,4]benzodiazepine;

2-Chloro-11,12-dihydro-12-methyl-(2-pyridyl)-9H,13aH-oxazolo-[3,2-d]-s-triazolo[4,3-a][1,4]benzodiazepine;

2-Chloro-11,12-dihydro-6-methyl-13a-(2-pyridyl)-9H,13aH-oxazolo(3,2-d]-s-triazolo[4,3-a][1,4]benzodiazepine;

2-Chloro-11,12-dihydro-6,11-dimethyl-13a-(2-pyridyl)-9H,13aH-oxazolo[3,2-d]-s-triazolo[4,3-a][1,4]benzodiazepine;

2-Chloro-11,12-dihydro-6,12-dimethyl-13a-(2-pyridyl)-9H,13aH-oxazolo[3,2-d]-s-triazolo[4,3-a][1,4]benzodiazepine;

11,12-Dihydro-13a-(2-pyridyl)-9H,13aH-oxazolo[3,2-d]-s-triazolo[4,3-a][1,4]benzodiazepine;

11,12-Dihydro-6-methyl-13a-(2-pyridyl)-9H,13aH-oxazolo-[3,2-d]-s-triazolo[4,3-a][1,4]benzodiazepine;

2,4-Dibromo-11,12-dihydro-6-methyl-13a-(2-pyridyl)-9H,13aH-oxazolo[3,2-d]-s-triazolo[4,3-a][1,4]benzodiazepine;

11,12-Dihydro-2,6-dimethyl-13a-(2-pyridyl)-9H,13aH-oxazolo[3,2-d]-s-triazolo[4,3-a][1,4]benzodiazepine;

11,12-Dihydro-6-methyl-2-nitro-13a-(2-pyridyl)-9H,13aH-oxazolo[3,2-d]-s-triazolo[4,3-a][1,4]benzodiazepine;

11,12-Dihydro-2-methoxy-6-methyl-13a-(2-pyridyl)-9H,13aH-oxazolo[3,2-d]-s-triazolo[4,3-a][1,4]benzodiazepine;

11,12-Dihydro-6-methyl-13a-(2-pyridyl)-2-trifuluoromethyl-9H,13aH-oxazolo[3,2-d]-s-triazolo[4,3-a][1,4]benzodiazepine.

COMPOUND (II)

4-[4-Bromo-2-(2-pyridinecarbonyl)phenyl]-3-chloromethyl-4H-1,2,4-triazole;
4-[4-Bromo-2-(2-pyridinecarbonyl)phenyl]-3-chloromethyl-5-methyl-4H-1,2,4-triazole;
4-[4-Bromo-2-(2-pyridinecarbonyl)phenyl]-3-chloromethyl-5-ethyl-4H-1,2,4-triazole;
4-[4-Bromo-2-(2-pyridinecarbonyl)phenyl]-3-chloromethyl-5-n-propyl-4H-1,2,4-triazole;
4-[4-Bromo-2-(2-pyridinecarbonyl)phenyl]-3-chloromethyl-5-isopropyl-4H-1,2,4-triazole;
4-[4-Bromo-2-(2-pyridinecarbonyl)phenyl]-5-n-butyl-3-chloromethyl-4H-1,2,4-triazole;
5-Benzyl-4-[4-bromo-2-(2-pyridinecarbonyl)phenyl]-3-chloromethyl-4H-1,2,4-triazole;
4-[4-Bromo-2-(2-pyridinecarbonyl)phenyl]-3-chloromethyl-5-phenyl-4H-1,2,4-triazole;
4-[4-Bromo-2-(2-pyridinecarbonyl)phenyl]-3-(1-chloroethyl)-4H-1,2,4-triazole;
4-[4-Bromo-2-(2-pyridinecarbonyl)phenyl]-3-(1-chloroethyl)-5-methyl-4H-1,2,4-triazole;
4-[4-Bromo-2-(4-pyridinecarbonyl)phenyl]-3-chloromethyl-4H-1,2,4-triazole;
4-[4-Bromo-2-(2-pyridinecarbonyl)phenyl]-3-bromomethyl-4H-1,2,4-triazole;
4-[4-Bromo-2-(2-pyridinecarbonyl)phenyl]-3-iodomethyl-4H-1,2,4-triazole;
4-[4-Bromo-2-(2-pyridinecarbonyl)phenyl]-3-fluoromethyl-4H-1,2,4-triazole;
4-[4-Bromo-2-(2-pyridinecarbonyl)phenyl]-3-sulfoxymethyl-4H-1,2,4-triazole;
4-[4-Bromo-2-(2-pyridinecarbonyl)phenyl]-3-methylsulfonyl-oxymethyl-4H-1,2,4-triazole;
4-[4-Bromo-2-(2-pyridinecarbonyl)phenyl]-3-phenylsulfonyl-oxymethyl-4H-1,2,4-triazole;
4-[4-Bromo-2-(2-pyridinecarbonyl)phenyl]-3-p-tolylsulfonyl-oxymethyl-4H-1,2,4-triazole;
4-[4-Chloro-2-(2-pyridinecarbonyl)phenyl]-3-chloromethyl-4H-1,2,4-triazole;
4-[4-Chloro-2-(2-pyridinecarbonyl)phenyl]-3-chloromethyl-5-methyl-4H-1,2,4-triazole;
4-[4-Chloro-2-(2-pyridinecarbonyl)phenyl]-3-chloromethyl-5-ethyl-4H-1,2,4-triazole;
4-[4-Chloro-2-(2-pyridinecarbonyl)phenyl]-3-chloromethyl-5-n-propyl-4H-1,2,4-triazole;
4-[4-Chloro-2-(2-pyridinecarbonyl)phenyl]-3-chloromethyl-5-isopropyl-4H-1,2,4-triazole;
5-n-Butyl-4-[4-chloro-2-(2-pyridinecarbonyl)phenyl]-3-chloromethyl-4H-1,2,4-triazole;
5-Benzyl-4-[4-chloro-2-(2-pyridinecarbonyl)phenyl]-3-chloromethyl-4H-1,2,4-triazole;
4-[4-Chloro-2-(2-pyridinecarbonyl)phenyl]-3-chloromethyl-5-phenyl-4H-1,2,4-triazole;
3-Chloromethyl-4-[4,6-dibromo-2-(2-pyridinecarbonyl)phenyl]-4H-1,2,4-triazole;
3-Chloromethyl-4-[4,6-dibromo-2-(2-pyridinecarbonyl)phenyl]-4H-1,2,4-triazole;
3-Chloromethyl-5-methyl-4-[4-methyl-2-(2-pyridinecarbonyl)phenyl]-4H-1,2,4-triazole;
3-Chloromethyl-4-[4-methoxy-2-(2-pyridinecarbonyl)phenyl]-5-methyl-4H-1,2,4-triazole;
3-Chloromethyl-5-methyl-4-[4-nitro-2-(pyridinecarbonyl)-phenyl]-4H-1,2,4-triazole;
3-Chloromethyl-5-methyl-4-[2-(2-pyridinecarbonyl)-phenyl-4-trifluoromethyl]-4H-1,2,4-triazole;
3-Chloromethyl-5-methyl-4-[2-(2-pyridinecarbonyl)-phenyl]-4H-1,2,4-triazole;
3-Chloromethyl-4-[2-(2-pyridinecarbonyl)phenyl]-4H-1,2,4-triazole.

The present invention is illustrated in more detail below with reference to the Examples, but the invention is not limited to these Examples.

EXAMPLE 1 a. A mixture of 8.7 g. of 2-(2-amino-5-bromobenzoyl)-pyridine, 5.7 g. of ortho-methyl acetate, 2.8 ml. of acetic acid and 100 ml. of benzene is refluxed, while removing alcohol produced by azeotropic distillation, for 1.5 hours and then cooled. The resultant mixture is washed with saturated aqueous sodium hydrogen carbonate solution, then with water, and dried over sodium sulfate. Evaporation of the solvent under reduced pressure gives 2-[2-(1-methoxyethylideneamino)-5-bromobenzoyl]pyridine as an oily product. This product is dissolved in 60 ml. of methanol, and to the solution are added 44 ml. of hydrazine hydrate (100 %) and 1.9 ml. of acetic acid. After stirring at room temperature for 3 hours, the resulting precipitate is collected by filtration, washed with methanol and dried to give 3-amino-6-bromo-3,4-dihydro-4-hydroxy-2-methyl-4-(2-pyridyl)quinazoline as crystals. Recrystallization from a mixture of methanol and chloroform gives colorless crystals melting at 208° to 210° C. (decomposition).

Elemental analysis for $C_{14}H_{13}BrN_4O$: Calculated: C 50.46, H 3.93, N 16.82. Found: C 50.02, H 3.70, N 17.11.

b. To a solution of 3.33 g. of the thus prepared 3-amino-6-bromo-3,4-dihydro-4-hydroxy-2-methyl-4-(2-pyridyl)-quinazoline in 30 ml. of dimethylformamide is added a solution of 0.51 g. of mono-chloroacetic acid anhydride in 6 ml. of dimethylformamide with stirring under ice-cooling. After the mixture is stirred for 30 minutes, to the resultant is added a solution of 4.2 g. of potassium carbonate in 250 ml. of water. The resulting mixture is filtered through a celite layer to remove insoluble material. The filtrate is extracted with ethyl acetate, and the ethyl acetate layer is washed with water, dried over sodium sulfate and then subjected to evaporation of the solvent. To the residue is added a mixture of ethyl acetate and ether, and the resulting precipitate is collected by filtration to give mono-(chloroacetyl) derivative of the starting compound as crystals. Recrystallization from ethyl acetate gives colorless prisms melting at 129° to 131° C. (decomposition).

Elemental analysis for $C_{16}H_{14}BrClN_4O_2$: Calculated: C 46.90, H 3.44, N 13.68. Found: C 47.07, H 3.20, N 13.61.

c. A solution of 2.17 g. of the mono-(chloroacetyl) derivative of 3-amino-6-bromo-3,4-dihydro-4-hydroxy-2-methyl-4-(2-pyridyl)quinazoline prepared in the experiment
b. in 30 ml. of acetic acid is heated at 80° C for 3 hours and then acetic acid is evaporated under reduced pressure. The residue is dissolved in chloroform, washed with saturated aqueous sodium hydrogen carbonate solution and water in this order and dried over sodium sulfate. After evaporation of the solvent under reduced pressure, the residue is washed with ethyl acetate and collected by filtration to give 4-[4-bromo-2-(2-pyridinecarbonyl)phenyl]-3-chloromethyl-5-methyl-4H-1,2,4-triazole as crystals. Recrystallization from a mixture of benzene-ether gives colorless prisms melting at 170° to 171.5° C. (decomposition).

Elemental analysis for $C_{16}H_{12}BrClN_4O$: Calculated: C 49.06, H 3.09, N 14.31. Found: C 48.85, H 2.89, N 14.15.

EXAMPLE 2 a. A mixture of 14 g. of 2-(2-amino-5-bromobenzoyl)-pyridine and 42 ml. of formic acid (99%) is refluxed for one hour and then the solvent is evaporated. The residue is neutralized with saturated aqueous sodium hydrogen carbonate solution and the precipitated crystals of 2-(5-bromo-2-formamidobenzoyl)pyridine are collected by filtration, followed by washing with water. Recrystallization from methanol gives yellow needles melting at 116° to 117° C.

Elemental analysis for $C_{13}H_9BrN_2O$: Calculated: C 51.17, H 2.97, N 9.18 Found: C 51.12, H 2.75, N 9.14 b. To a solution of 11.2 g. of the 2-(5-bromo-2-formamidobenzoyl)pyridine prepared in the experiment (a) in 50 ml. of methanol is added 10 ml. of hydrazine hydrate (100 %). The resulting mixture is heated at 60° C for several minutes and thereafter left to stand at room temperature for 5 hours. The resulting precipitate is collected by filtration and washed with methanol and ether and dried to give 3-amino-6-bromo-4-hydroxy-4-(2-pyridyl)-3,4-dihydroquinazoline as colorless granules melting at 185° to 187° C. (decomposition).

Elemental analysis for $C_{13}H_{11}BrN_4O$: Calculated: C 48.92, H 3.47, N 17.55. Found: C 48.77, H 3.35, N 17.56.

c. To 8.5 g. of the 3-amino-6-bromo-4-hydroxy-4-(2-pyridyl)-3,4-dihydroquinazoline prepared in the experiment b. are added 60 ml. of chloroform and a solution of 11.3 g. of sodium carbonate in 110 ml. of water. To the resulting mixture is added dropwise 12 g. of monochloroacetyl chloride under stirring at 10° to 15° C., and the mixture is stirred at the same temperature for 30 minutes. After stirring is continued for further 30 minutes, the precipitated crystals are collected by filtration, followed by washing with chloroform and water in this order and dried to give di-(chloroacetyl) derivative of the starting compound as crystals. Recrystallization from chloroform-methanol gives colorless prisms melting at 148.5° to 149° C. (decomposition).

Elemental analysis for $C_{17}H_{13}BrCl_2N_4O_3$: Calculated: C 43.24, H 2.77, N 11.86. Found: C 42.80, H 2.48, N 11.47.

d. A mixture of a solution of 0.94 g. of the thus obtained di-(chloroacetyl) derivative of 3-amino-6-bromo-4-hydroxy-4 -(2-pyridyl)-3,4-dihydroquinazoline in 19 ml. of benzene and 0.4 g. of monochloro acetic acid is refluxed for 30 minutes. Then, the benzene layer is washed with water. After evaporation of benzene under reduced pressure, the residue is washed with a mixture of methanol and isopropyl ether to give 4-[4-bromo-2-(2-pyridinecarbonyl)phenyl]-3-chloromethyl-4H-1,2,4-triazole as crystals. Recrystallization from ethyl acetate gives colorless crystals melting at 146° to 147° C.

Elemental analysis for $C_{15}H_{10}BrClN_4O$: Calculated: C 47.70, H 2.66, N 14.83. Found: C 47.86, H 2.43, N 14.83.

EXAMPLE 3

To a solution of 0.7 g. of 8-bromo-1-methyl-6-(2-pyridyl)-4H-s-triazolo[4,3-a][1,4]benzodiazepine in 5 ml. -pyridinecarbonyl)phenyl]of 6 N-hydrochloric acid is added a solution of 1.25 g. of sodium nitrite in 2.5 ml. of water at 5° to 10° C. under ice-cooling. After stirring the mixture for one hour under cooling and another two hours at room temperature, the resulting mixture is neutralized with saturated aqueous sodium hydrogen carbonate solution and then extracted with chloroform. The chloroform layer is washed with water and dried over sodium sulfate. Evaporation of the solvent gives a mixture of 4-[4-bromo-2-(2-pyridinecrbonyl)phenyl]-3-hydroxymethyl-5-methyl-4H-1,2,4-triazole and 4-[4-bromo-2-(2-pyridinecarbonyl)phenyl]-3-chloromethyl-4H-1,2,4-triazole.

The mixture is dissolved in 20 ml. of chloroform and 4.0 ml. of thionyl chloride is added to the resulting solution. After the whole mixture is stirred at room temperature for 3 hours, the solvent is evaporated. To the residue is added saturated aqueous sodium hydrogen carbonate solution, and the whole mixture is extracted with chloroform. The chloroform layer is washed with water and dried over sodium sulfate. Evaporation of the solvent gives 4-[4-bromo-2-(2-pyridinecarbonyl)phenyl]-3-chloromethyl-5-methyl-4H-1,2,4-triazole as colorless crystals melting at 172° to 173° C. (decomposition). This product is identical with that obtained in Example 1 (c) with respect to its infra-red absorption spectrum.

The 3-hydroxymethyl derivative produced in the above experiment can be easily separated from the mixture of that and 3-chloromethyl derivative by subjecting the mixture to silica gel-column chromatography using a mixture of chloroform-ethyl acetate-methanol (85:10:5) as an eluant. Recrystallization of the 3-hydroxymethyl derivative from methanol gives colorless prisms melting at 203° to 205° C. (decomposition).

EXAMPLE 4

To a solution of 2.50 g. of 8-bromo-6-(2-pyridyl)-4H-s-triazolo[4,3-a][1,4]benzodiazepine in 20 ml. of 6 N-hydrochloric acid is added a solution of 5.0 g. of sodium nitrite in 10 ml. of water at 5° to 10° C. under ice-cooling. After stirring the mixture at the same temperature for 1.5 hours, the resulting mixture is neutralized with saturated aqueous sodium hydrogen carbonate solution and extracted with chloroform. The chloroform layer is washed with water and dried over sodium sulfate. Evaporation of the solvent gives a mixture of 4-[4-bromo-2-(2-pyridinecarbonyl)phenyl]-3-hydroxymethyl-4H-1,2,4-triazole and 4-[4-bromo-2-(2-pyridinecarbonyl)phenyl]-3-chloromethyl-4H-1,2,4-triazole. The mixture is dissolved in 50 ml. of chloroform and then 14 ml. of thionyl chloride is added to the solution. After the mixture is stirred at room temperature for 2 hours, the solvent is evaporated. The residue is neutralized with saturated aqueous sodium hydrogen carbonate solution, and extracted with chloroform. The chloroform layer is washed with water and dried over sodium sulfate. Evaporation of the solvent gives 4-[4-bromo-2-(2-pyridinecarbonyl)phenyl]-3-chloromethyl-4H-1,2,4-triazole as colorless crystals, melting at 147° to 149° C. This product is identical with that obtained in Example 2 (d) with respect to its infra-red absorption spectrum.

EXAMPLE 5

According to the similar procedure as described in Example 4, the reaction product of 8-bromo-1-ethyl-6-(2-pyridyl)-4H-s-triazolo[4,3-a][1,4]benzodiazepine and 6 N hydrochloric acid-sodium nitrite is chlorinated with thionyl chloride to give 4-[4-bromo-2-(2-pyridinecarbonyl)-phenyl]-3-chloromethyl-5-ethyl-4H-1,2,4-triazole as crystals. Recrystallization from acetone gives pale yellow prisms melting at 199° to 201° C. (decomposition).

EXAMPLE 6

A mixture of a solution of 0.3 g. of 4-[4-bromo-2-(2-pyridinecarbonyl)phenyl]-3-chloromethyl-5-methyl-4H-1,2,4-triazole in 5 ml. of ethanol and 0.3 ml. of ethanolamine is refluxed for 10 hours. After evaporation of the solvent under reduced pressure, the residue is diluted with water and the resulting crystals are collected by filtration to give 2-bromo-11,12-dihydro-6-methyl-13a-(2-pyridyl)-9H,13aH-oxazolo[3,2-d]-s-triazolo[4,3-a][1,4]benzodiazepine. Recrystallization from ethanol gives colorless prisms melting at 268° to 269° C. (decomposition).

Elemental analysis for $C_{18}H_{16}BrN_5O$: Calculated: C 54.28, H 4.05, N 17.59. Found: C 54.05, H 4.02, N 17.54.

According to the similar procedure as described in the foregoing Example 6, the following compounds can be produced from corresponding 4-(2-pyridinecarbonylphenyl)-3-halomethyl-4H-1,2,4-triazole and alkanol amine or alkylene diamine:

2-bromo-11,12-dihydro-13a-(2-pyridyl)-9H,13aH-oxazolo[3,2-d]-s-triazolo[4,3-a][1,4]benzodiazepine: colorless prisms (recrystallized from methanol) melting at 265° to 267° C. (decomposition);

2-bromo-6-ethyl-11,12-dihydro-13a-(2-pyridyl)-9H,13aH-oxazolo[3,2-d]-s-triazolo[4,3-a][1,4]benzodiazepine: colorless needles (recrystallized from acetone) melting at 287° to 289° C. (decomposition);

2-bromo-11,12-dihydro-12-methyl-13a-(2-pyridyl)-9H,13aH-oxazolo[3,2-d]-s-triazolo[4,3-a][1,4]benzodiazepine: colorless prisms (recrystallized from acetone) melting at 247 to 249° C. (decomposition);

2-bromo-11,12-dihydro-6,12-dimethyl-13a-(2-pyridyl)-9H,13aH-oxazolo[3,2-d]-s-triazolo[4,3-a][1,4]benzodiazepine: colorless prisms (recrystallized from acetone) melting at 233° to 235° C. (decomposition);

2-bromo-12,13-dihydro-14a-(2-pyridyl)-9H,11H,14aH-[1,3]oxazino[3,2-d]-s-triazolo[4,3-a][1,4]benzodiazepine: colorless prisms (recrystallized from acetone) melting at 238° to 239° C. (decomposition);

2-bromo-12,13-dihydro-6-methyl-14a-(2-pyridyl)-9H,11H,14aH-[1,3]oxazino[3,2-d]-s-triazolo[4,3-a][1,4]-benzodiazepine: colorless prisms (recrystallized from acetone) melting at 243° to 245° C. (decomposition); and 2-bromo-11,12,13,13a-tetrahydro-6-methyl-13a-(2-pyridyl)-9H-imidazo[1,2-d]-s-triazolo[4,3-a][1,4]benzo-diazepine: colorless prisms (recrystallized from acetone) melting at 245° to 246° C.

EXAMPLE 7

An example of a suitable composition in which a compound of this invention is utilized as tranquilizer is as follows:

| | Tablet | | |
|---|---|---|---|
| (1) | 2-bromo-11,12-dihydro-6,12-dimethyl-13a-(2-pyridyl)-9H,13aH-oxazolo[3,2-d]-s-triazolo[4,3-a][1,4]benzodiazepine | 1 | mg |
| (2) | lactose | 73 | mg |
| (3) | corn starch | 40 | mg |
| (4) | hydroxypropyl cellulose | 5.5 | mg |
| (5) | magnesium stearate | 0.5 | mg |
| | | 120.0 | mg |
| | | per tablet | |

(1), (2), 9/10 quantity of (3), and (4) are thoroughly mixed and the mixture is granulated by wet granulation method. Remaining quantity of (3), and (5) are added to the granules and compressed into tablets. Thus prepared tablets may further be coated with suitable coating materials, e.g. sugar.

What we claim is:
1. A heterocyclic compound of the general formula

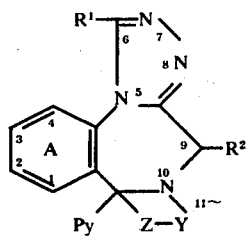

wherein $R^1$ represents a hydrogen atom or a straight chain alkyl, branched alkyl or cyclic alkyl, said alkyl groups having up to 6 carbon atoms, a benzyl, phenethyl, phenyl, tolyl or naphthyl group; $R^2$ represents hydrogen atom or a lower alkyl group having 1 to 4 carbon atoms; Py represents a pyridyl group; Y represents an ethylene or a trimethylene group which may have lower alkyl group as substituent; Z represents an oxygen atom, a sulfur atom or —NH-group; and the ring A is either unsubstituted or substituted by a halogen atom, nitro, alkyl, alkoxy or trifluoromethyl group, said alkyl or alkoxy group containing from 1 to 4 carbon atoms.

2. A compound as claimed in claim 1, wherein $R^1$ is hydrogen.

3. A compound as claimed in claim 1, wherein $R^1$ is a lower alkyl group having 1 to 3 carbon atoms.

4. A compound as claimed in claim 1, wherein $R^2$ is hydrogen.

5. A compound as claimed in claim 1, wherein ring A is unsubstituted.

6. A compound as claimed in claim 1, wherein the ring A is substituted by a halogen atom.

7. A compound as claimed in claim 1, wherein Z is oxygen.

8. A compound as claimed in claim 1, wherein Z is —NH—.

9. A compound as claimed in claim 2, wherein $R^2$ is hydrogen.

10. A compound as claimed in claim 9, wherein ring A is unsubstituted.

11. A compound as claimed in claim 9, wherein ring A is substituted by a halogen atom.

12. A compound as claimed in claim 11, wherein the halogen atom is substituted in the 2-position of the ring A.

13. A compound as claimed in claim 10, wherein Py is a 2-pyridyl group.

14. A compound as claimed in claim 12, wherein the halogen atom is bromine.

15. A compound as claimed in claim 13, wherein Z is oxygen atom.

16. A compound as claimed in claim 15, wherein Y is ethylene, trimethylene or propylene.

17. A compound according to claim 1, which is 2-bromo-11,12-dihydro-6-methyl-13a-(2-pyridyl)-9H,13aH-oxazolo[3,2-d]-s-triazolo[4,3-a][1,4]benzodiazepine.

18. A compound according to claim 1, which is 2-bromo-11,12-dihydro-13a-(2-pyridyl)-9H,13aH-oxazolo[3,2-d]-s-triazolo[4,3-a][1,4]benzodiazepine.

19. A compound according to claim 1, which is 2-bromo-6-ethyl-11,12-dihydro-13a-(2-pyridyl)-9H,13aH-oxazolo[3,2-d]-s-triazolo[4,3-a][1,4]benzodiazepine.

20. A compound according to claim 1, which is 2-bromo-11,12-dihydro-12-methyl-13a-(2-pyridyl)-9H,13aH-oxazolo-[3,2-d]-s-triazolo[4,3-a][1,4]benzodiazepine.

21. A compound according to claim 1, which is 2-bromo-11,12-dihydro-6,12-dimethyl-13a-(2-pyridyl)-9H,13aH-oxazolo-[3,2-d]-s-triazolo[4,3-a][1,4]benzodiazepine.

22. A compound according to claim 1, which is 2-bromo-12,13-dihydro-14a-(2-pyridyl)-9H,11H,14aH-[1,3]oxazino-[3,2-d]-s-triazolo[4,3-a][1,4]benzodiazepine.

23. A compound according to claim 1, which is 2-bromo-12,13-dihydro-6-methyl-14a-(2-pyridyl)-9H,11H,14aH-[1,3]-oxazino[3,2-d]-s-triazolo[4,3-a][1,4]benzodiazepine.

24. A compound according to claim 1, which is 2-bromo-11,12,13,13a-tetrahydro-6-methyl-13a-(2-pyridyl)-9H-imidazo-[1,2-d]-s-triazolo[4,3-a][1,4]benzodiazepine.

25. A pharmaceutical composition useful as a muscle relaxant, anti-convulsant, sedative or tranquilizer, comprising an effective amount of a compound as claimed in claim 1 together with a pharmaceutically acceptable carrier or diluent therefor.

26. A compound according to claim 1 wherein $R^1$ is hydrogen or an alkyl group having 1 to 3 carbon atoms.

27. A compound according to claim 1 wherein A is unsubstituted, or substituted by bromo, chloromethyl, nitro, methoxy, or trifluoromethyl; $R^1$ is hydrogen, methyl, ethyl, n-propyl, i-propyl, n-butyl, phenyl or benzyl; $R^2$ is hydrogen or methyl; Z is oxygen, sulfur or —NH—; Y is ethylene, which may be substituted by methyl, or trimethylene when Z is oxygen, ethylene when Z is sulfur, or ethylene when Z is —NH—; and Py is 2-pyridyl or 4-pyridyl.

* * * * *

UNITED STATES PATENT OFFICE
CERTIFICATE OF CORRECTION

Patent No. 4,013,763                    Dated   March 22, 1977

Inventor(s)   Yutaka Kuwada, et al

It is certified that error appears in the above-identified patent and that said Letters Patent are hereby corrected as shown below:

In the Abstract, 6th line below formula: "groups" should read --group--.

Column 6, line 1: "2-Bromo-11, 12-dihydro-6-ethyl-13a-(2;1-pyridyl)-" should read -- 2-Bromo-11,12-dihydro-6-ethyl-13a-(2-pyridyl)- --.

Column 8, lines 57 through 68: These lines should not be a separate paragraph but should continue from line 56 following "periment".

Column 9, lines 34 through 45: These lines should not be a separate paragraph but should continue from line 33 following "iment".

line 68: "ml.-pyridinecarbonyl)phenyl] of 6 N-hydrochloric" should read -- ml. of 6 N-hydrochloric --.

UNITED STATES PATENT OFFICE
CERTIFICATE OF CORRECTION

Patent No. 4,013,763             Dated March 22, 1977

Inventor(s)  Yutaka Kuwada, et al

It is certified that error appears in the above-identified patent and that said Letters Patent are hereby corrected as shown below:

Column 10, line 9: "4-[4-bromo-2-(2-pyridine crbonyl)phenyl]-" should read -- 4-[4-bromo-2-(2-pyridine carbonyl)phenyl]- --.

Signed and Sealed this

Eighteenth Day of April 1978

[SEAL]

Attest:

RUTH C. MASON
Attesting Officer

LUTRELLE F. PARKER
Acting Commissioner of Patents and Trademarks